United States Patent [19]

Hosotte-Filbert et al.

[11] Patent Number: 5,681,877
[45] Date of Patent: Oct. 28, 1997

[54] USE OF ACRYLIC BLOCK COPOLYMERS AS WETTING AND/OR DISPERSING AGENTS FOR SOLID PARTICLES, AND RESULTING DISPERSIONS

[75] Inventors: Claude Hosotte-Filbert, Belfort; Carole Tondeur; Henri-Gérard Riess, both of Mulhouse; Alain Meybeck, Courbevoie; Jean-François Tranchant, Boigny-sur-Bionne, all of France

[73] Assignee: LVMH Recherche, France

[21] Appl. No.: 619,632

[22] PCT Filed: Sep. 28, 1994

[86] PCT No.: PCT/FR94/01132

§ 371 Date: Mar. 27, 1996

§ 102(e) Date: Mar. 27, 1996

[87] PCT Pub. No.: WO95/09207

PCT Pub. Date: Apr. 6, 1995

[30] Foreign Application Priority Data

Sep. 30, 1993 [FR] France ................. 93 11691

[51] Int. Cl.[6] ..................................... C08L 1/08
[52] U.S. Cl. ............... 524/32; 523/204; 523/205; 524/31; 524/315; 524/413; 524/425; 524/430; 524/431; 524/432; 524/492; 524/493; 524/497; 524/505; 524/533
[58] Field of Search ................. 524/431, 497, 524/315, 31, 32, 505, 533, 492, 493, 413, 425, 430, 432; 523/204, 205

[56] References Cited

U.S. PATENT DOCUMENTS

| | | | |
|---|---|---|---|
| 4,060,511 | 11/1977 | Sinclair et al. | 524/533 X |
| 4,234,466 | 11/1980 | Takahashi et al. | 524/533 X |
| 4,365,035 | 12/1982 | Zabiak | 524/497 X |
| 4,421,881 | 12/1983 | Benkendorf et al. | 524/32 X |
| 4,476,257 | 10/1984 | Ishino et al. | 524/32 X |
| 4,659,769 | 4/1987 | Ohmura et al. | 524/533 X |
| 5,085,698 | 2/1992 | Ma et al. | 106/20 |
| 5,200,456 | 4/1993 | Teyssie et al. | 524/505 X |
| 5,231,131 | 7/1993 | Chu et al. | 524/533 X |
| 5,272,201 | 12/1993 | Ma et al. | 524/533 X |
| 5,519,085 | 5/1996 | Ma | 524/505 X |

FOREIGN PATENT DOCUMENTS

| | | |
|---|---|---|
| 2185656 | 1/1974 | France . |
| 4218734 | 12/1992 | Germany . |
| 2005697 | 4/1979 | United Kingdom . |

OTHER PUBLICATIONS

Macromolecules, vo. 24, 1991, US, pp. 4997–5000, Varshney et al 'Anionic Polymerization of Acrylic Monomers'.

*Primary Examiner*—Judy M. Reddick
*Attorney, Agent, or Firm*—Bierman, Muserlian and Lucas

[57] ABSTRACT

Block copolymers denoted by AB from acrylic or methacrylic acid, the corresponding blocks being denoted by A, and from alkyl acrylate or methacrylate with the alkyl chain being $C_1$–$C_{10}$, the corresponding blocks being denoted by B. Said copolymer blocks are used as wetting and/or dispersing agents for solid particles in an essentially organic medium consisting of a solvent or a mixture of solvents solubilizing the block B.

The invention also concerns solid particle dispersions using the above-defined block copolymers.

It also concerns compositions, in particular cosmetic compositions, containing said dispersions.

38 Claims, 4 Drawing Sheets

FIG_1

FIG_2a

FIG_2b

FIG_2c

FIG_3

FIG_4

FIG_5

USE OF ACRYLIC BLOCK COPOLYMERS AS WETTING AND/OR DISPERSING AGENTS FOR SOLID PARTICLES, AND RESULTING DISPERSIONS

The present invention relates to a novel use of acrylic block copolymers as wetting and/or dispersing agents for solid particles, and to dispersions of solid particles containing these block copolymers.

The use of macromolecular surfactants for treating surfaces in non-aqueous media has formed the subject of numerous studies, particularly laboratory studies aimed at specifying the mechanism and kinetics of the fixing of polymers to the surface of particular powders.

The following may be mentioned as examples of such studies:

- studies using a variety of block copolymers denoted symbolically by A-b-B, A and B representing the two blocks and b indicating that block copolymers are involved;
- the work of Du Pont de Nemours on a silica dispersed in isopropanol with the aid of block copolymers based on butyl methacrylate and dimethylaminoethyl methacrylate (Wu, Yokoyama, Setterquist, Polym. J. (91) vol. 23, page 409);
- the work of Molau and Richardson on titanium oxide dispersed by polystyrene-b-polybutadiene copolymers (Adv. Chem. Ser. (71), vol. 99, page 379);
- various studies on silicas in the presence of polystyrene-b-polyvinylpyridine copolymers in toluene, for example: J. F. Tassin, R. L. Siemens, Wing T. Tang, G. Hadziioannou, J. D. Swales, B. A. Smith, J. Phys. Chem. 1989, 93, 2106–2111;
- the work of Leemans, Fayt, Teyssié, Uijtterhoeven, Polymer (90), vol. 31, page 108, on the dispersion of carbon black by polystyrene-b-polystearyl methacrylate copolymers; and
- studies using random-type copolymers, an example which may be mentioned being the study of the adsorption onto $TiO_2$ of random amphiphilic copolymers having a skeleton consisting of methyl methacrylate and acrylonitrile and carrying heptameric grafts of hydroxystearic acid, said study being published in J. of Colloid and Interface Sci., 26, 214–221 (1968).

Block copolymers are known between acrylic or methacrylic acid (symbolized by the block A) and alkyl acrylate or methacrylate (symbolized by the block B), the alkyl chain being between C1 and C10. These copolymers can be of the two-block type (A-b-B) or three-block type (A-b-B-b-A or B-b-A-b-B). They are symbolized hereafter by AB irrespective of whether they are two-block or three-block. Their synthesis is described in particular by:

S. K. Varshney, C. Jacobs, J.-P. Hautekcer, P. Bayard, R. Jérôme, R. Fayt, P. Teyssié, Macromolecules, vol. 24, p. 4997–5000 (1991), for two-block and three-block acrylic acid/methyl methacrylate copolymers;

T. E. Long, C. D. DePorter, N. Patel, D. W. Dwight, G. L. Wilkes, J. E. McGrath, Polym. Prep., vol. 28(2), p. 214–216 (1987), for two-block methacrylic acid/2-ethylhexyl methacrylate copolymers;

C. D. DePorter, T. E. Long, L. N. Venkateshwaran, G. L. Wilkes, J. E. McGrath, Polym. Prep., vol. 29(1), p. 343–345 (1988), for three-block methacrylic acid/2-ethylhexyl methacrylate copolymers;

C. D. DePorter, L. N. Venkateshwaran, G. A. York, G. L. Wilkes, J. E. McGrath, Polym. Prep., vol. 30(1), p. 210–203 (1989), for two-block and three-block methacrylic acid/n-hexyl methacrylate copolymers.

The process described makes it possible to vary the nature and length of each of the polymer blocks by adjusting the concentration of initiator and monomers.

The Applicant has now discovered that this family of acrylic copolymers, symbolized hereafter by AB, and particularly PAA-b-PMMA, can advantageously be used to modify the surface energy of solid particles relative to organic liquids, resulting in their use as wetting and/or dispersing agents for these particles in organic media in order to obtain stable dispersions. Thus the use of these block copolymers provides an advantageous solution to the problem of the formation of aggregates of particles when attempting to form stable dispersions of these particles in a solvent.

Thus, according to one of its essential characteristics, the invention relates to the use of block copolymers, symbolized by AB, of acrylic or methacrylic acid, the corresponding block(s) being symbolized by A, and of alkyl acrylate or methacrylate with the alkyl chain being between $C_1$ and $C_{10}$, the corresponding block(s) being symbolized by B, as wetting and/or dispersing agents for solid particles in an essentially organic medium consisting of a solvent or solvent mixture solubilizing the block B.

In the present description, essentially organic medium is understood as meaning a medium containing less than 5% of water and preferably less than 1% of water.

For the different copolymers of the family, depending on the nature of the medium in which it is desired to disperse the powder, and on the nature of the powder, the Applicant's studies have led it:

- on the one hand to determine the adsorption factor of the copolymer, defined as the ratio of the amount of "fixed" copolymer to the initial amount. "Fixed" copolymer is understood as meaning copolymer adsorbed by physical bonds onto the surface of the solid particle;
- and on the other hand to determine the efficacy of the wetting agent.

The Applicant's studies have led it in particular to demonstrate the existence of a plateau in the curves, called adsorption isotherms, which represent the adsorption rate of the copolymer as a function of the initial concentration of the copolymer at a given temperature.

The efficacy of the wetting and/or dispersing agent will be characterized by the minimum amount of copolymer which has to be used to reach the plateau of the adsorption isotherm and cover the entire surface of the particle.

The Applicant's studies have led it to demonstrate the significant reduction in the surface energy of the solid particles, in the amount of aggregates formed between the particles and in their size, in the presence of block copolymer AB in the medium.

The Applicant has also demonstrated that the acrylic copolymers AB constitute remarkable stabilizers for dispersions of solid particles in organic media and make it possible in particular to obtain dispersions whose supernatant does not become limpid for at least 24 h in the case of copolymer contents corresponding to the plateau of the adsorption isotherm.

The block copolymers of the AB type defined above are advantageously two-block copolymers symbolized by A-b-B.

They can also be three-block copolymers of the A-b-B-b-A or B-b-A-b-B type.

According to one particularly advantageous variant of the invention, the chosen copolymers are two-block copolymers of acrylic acid (symbolized by AA) and methyl methacrylate (symbolized by MMA), represented by PAA-b-PMMA.

The solid particles can be of any type and advantageously have dimensions of between a few nanometers and a few millimeters, preferably of between 50 nm and 100 µm.

In particular, they can be mineral particles, especially particles consisting of metal oxides, for example titanium, zinc, iron or zirconium oxide, silica, alumina or calcium carbonate.

These particles can be pigments which may or may not be fixed to a mineral or organic support.

The invention is very particularly applicable to mineral pigments.

Examples of pigments which may be mentioned are titanium oxide, iron oxide, zinc oxide and azo colorants in the form of calcium or barium lake.

The mineral supports can consist of alumina, silica or else $TiO_2$.

The acrylic block copolymers AB used according to the invention as dispersing and/or wetting agents for solid particles in an organic medium, particularly the copolymers PAA-b-PMMA, advantageously have a number-average molecular weight ($M_n$) of between 2000 and 500,000, preferably of between 2000 and 100,000.

The block A, particularly PAA, of these copolymers represents from 5 to 95% by weight of the copolymer in order to obtain a wetting effect.

To obtain a dispersing effect as well, resulting in a stable dispersion, the block A preferably represents less than 50% by weight of the copolymer.

The organic solvent used to treat the particles can be:
any solvent for both the blocks A and B,
any solvent for the block B and non-solvent for the block A,
any mixture of solvents which solubilizes both the blocks, or
any mixture of solvents which solubilizes the block B but does not solubilize the block A.

The following are examples of solvents which can be used in the case of the copolymers PAA-b-PMMA:
dioxane, dimethylformamide or dimethyl sulfoxide as a solvent for both the blocks, any solvent for the PMMA block, i.e., for example, esters such as methyl, ethyl, propyl, butyl or amyl acetate, ketones such as acetone, methyl ethyl ketone, methyl butyl ketone or cyclohexanone, chlorinated solvents such as chloroform or dichloromethane, aromatics, for example toluene or xylene, or acetic acid, or mixtures of the above solvents or mixtures of a solvent for PMMA with a non-solvent for PMMA in proportions which keep this block soluble, such as, for example, a butyl acetate/ethanol or isopropanol mixture containing at least 50% of butyl acetate.

According to another of its features, the invention relates to stable dispersions of solid particles in a solvent or a mixture of solvents, in which dispersions the dispersing agent is an acrylic block copolymer AB as defined above, particularly a copolymer PAA-b-PMMA, and the solvent is an essentially organic medium solubilizing the block B.

The particles which can be used to prepare the dispersions according to the invention are any particles as defined above, particularly solid particles with dimensions of between a few nanometers and a few millimeters, preferably of between 50 nm and 100 µm.

The invention is very particularly applicable to the dispersion of mineral solid particles, particularly particles of metal oxides and more particularly mineral pigments which may or may not be supported on an organic or mineral support.

Among the dispersions of the invention, dispersions of titanium oxide particles may be mentioned very particularly.

The copolymers which can be used to prepare the dispersions according to the invention are all the block copolymers of the AB type defined above, particularly the copolymers PAA-b-PMMA, advantageously those with a number-average molecular weight of between 2000 and 500,000, preferably of between 2000 and 100,000.

The block A, particularly PAA, represents from b 5to 95% by weight of the block copolymer, preferably less than 50% by weight of said block copolymer.

The dispersions according to the invention contain from 0.1 to 30% by weight of block copolymer, based on the solid particles, preferably from 0.5% to 15% (depending on the specific surface area of the solid particles).

The essentially organic media used to prepare the dispersions according to the invention can be:
any solvent for both the blocks A and B,
any solvent for the block B and non-solvent for the block A,
any mixture of solvents which solubilizes both the blocks, or
any mixture of solvents which solubilizes the block B but does not solubilize the block A.

The following are examples of solvents which can be used in the case of the copolymers PAA-b-PMMA:
dioxane, dimethylformamide or dimethyl sulfoxide as a solvent for both the blocks, any solvent for the PMMA block, i.e., for example, esters such as methyl, ethyl, propyl, butyl or amyl acetate, ketones such as acetone, methyl ethyl ketone, methyl butyl ketone or cyclohexanone, chlorinated solvents such as chloroform or dichloromethane, aromatics, for example toluene or xylene, or acetic acid, or mixtures of the above solvents or mixtures of a solvent for PMMA with a non-solvent for PMMA in proportions which keep this block soluble, such as, for example, a butyl acetate/ethanol or isopropanol mixture containing at least 50% of butyl acetate.

Esters, for example butyl, propyl or ethyl acetate, or ester/alcohol mixtures made up predominantly of esters are advantageously chosen as the solvent or solvent mixture.

A particularly useful solvent for preparing the dispersions of the invention is butyl acetate. It is also advantageous to use butyl acetate/ethanol mixtures containing at least 50% of butyl acetate.

The invention is very particularly applicable to the dispersion of titanium oxide particles, particularly particles with dimensions of between 50 nm and 1 µm.

In practice, the adsorption factor is determined as follows: a weight $m_s$ of solution of initial copolymer concentration Ci is brought into contact with a weight $m_c$ of particles of specific surface area S. Following adsorption, the new concentration (Ce) of the solution is determined after removal of the particles by centrifugation. The adsorption factor (AF) is given by the formula $$AF=(Ci-Ce)/Ci \times 100 \ (\%)$$

The adsorption rate ($\Gamma$) is in turn given by:

$$\Gamma=[(Ci-Ce) \times m_s]/m_c \times S$$

Experiments show that a small amount of copolymers is sufficient to disperse a load correctly. For example, in the case of a weight of 1 g of titanium oxide powder of 10 m²/g, using butyl acetate as the solvent, about 40 mg of copolymer PAA-b-PMMA of number-average molecular weight ($M_n$) of 9900, containing 22% by weight of PAA, are required to reach the plateau of the adsorption isotherm at 20° C.

The dispersibility is evaluated from particle size measurements, for example using an apparatus of the Coulter LS130 type.

One particular advantage of the block copolymers used as dispersing agents according to the invention is that they produce stable dispersions.

The stabilization of the dispersions is assessed either by measuring the sedimentation rate of the suspensions as a function of time, or by following the variations in the absorbance of the supernatant as a function of centrifugation time.

Another advantage of the dispersions according to the invention is that if decantation takes place over time, the deposit formed is still readily redispersible in the medium after shaking, the copolymer totally covering the surface of the particle and thereby preventing it from aggregating.

Another advantage of the dispersions according to the invention is that when they are dried at room temperature, the powder recovered can readily be redispersed afterwards in the solvent.

According to another of its essential characteristics, the invention further relates to any composition containing the dispersions described above. It relates very particularly to the compositions containing pigment dispersions which are intended for the paint or cosmetics sector.

One particular advantage of the dispersions according to the invention in which it is the B blocks, particularly the PMMA blocks, which are the stabilizing blocks is that they are compatible with nitrocellulose, enabling them to be used in particular in the preparation of nail varnishes.

The Examples which follow are given purely in order to illustrate the invention.

EXAMPLES

Example 1

Dispersion of a Titanium Oxide Powder

The copolymer used is a PAA-b-PMMA of $M_n$=9900, containing 22% Of PAA.

The solvent is butyl acetate.

The copolymer is dissolved in butyl acetate. 3 g of titanium oxide of specific surface area 10 m²/g are then added to 10 g of solution and the mixture is shaken for 24 h.

Figure 1:
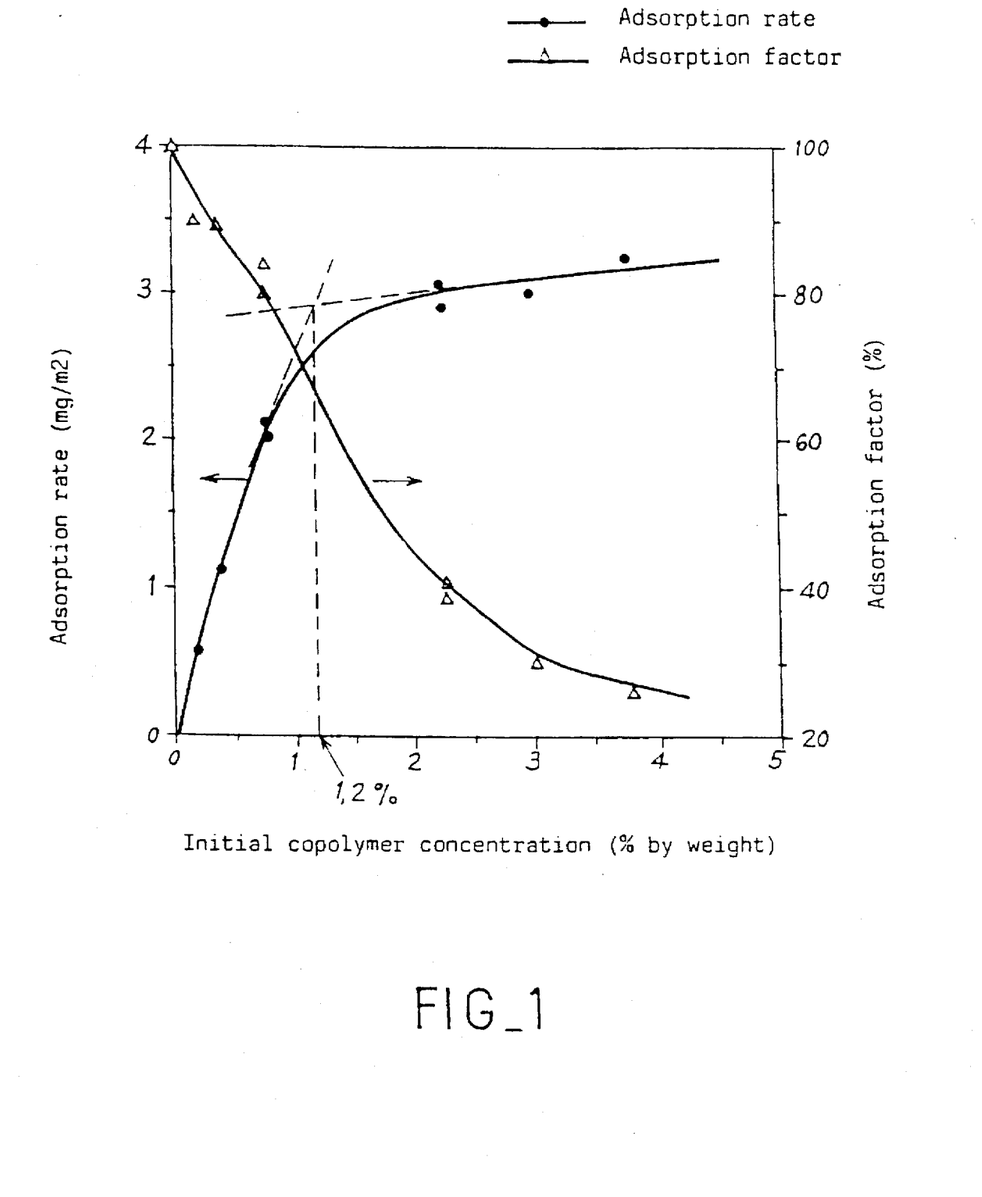
FIG. 1 illustrates the adsorption isotherm for a dispersion at different initial concentrations of copolymer.

FIG. 1 gives the adsorption rate and the adsorption factor as a function of the initial copolymer concentration, expressed in percentages by weight. The adsorption factor, AF, is given by the relation ship:

$$AF=(Ci-Ce)/Ci \times 100 \ (\%)$$

where Ci is the initial copolymer concentration and Ce is the concentration of the solution after it has been brought into contact with the solid particles and the solid particles have been separated off by centrifuga tion.

The adsorption rate is given by $$\Gamma=[(Ci-Ce)M_s]/m_c S$$

where $m_s$ is the weight of solution and $m_c$ is the weight of $TiO_2$ of specific surface area S.

In the present case:
$m_s$=10 g
S=10 m²/g
$m_c$=3 g.

The plot of the curve in FIG. 1, giving the adsorption rate as a function of the initial copolymer concentration at 20° C. (adsorption isotherm), clearly shows the existence of a plateau, the start of which is determined by drawing the tangents as indicated in FIG. 1.

In the particular case of this Example, the start of the plateau determined on the curve corresponds to an initial copolymer concentration of 1.2% by weight.

Calculation then shows that 40 mg are required in this case in order to stabilize and disperse 1 g of $TiO_2$.

Example 2

Demonstration of the Modification of Surface Energy

For the $TiO_2$ treated with copolymers PAA-b-PMMA by the procedure described in Example 1, the modification of surface energy is estimated by Stevens' test as described by P. Stevens, L. Gypen and R. Jennen-Bartholomeussen in "Wettability of powders" Farmaceutisch Tijdschrift voor Belgïe, 51e jaargang, nummer 2, Maart–April 1974.

Before treatment, the $TiO_2$ has a surface energy of about 70 mJ/m², i.e. a pronounced hydrophilic character. After adsorption of the copolymer (Ci=3%), a sharp decrease in surface energy down to a value of about 40 mJ/m² is observed.

These observations are confirmed by reversed-phase gas chromatography at infinite dilution.

Example 3

Demonstration of the Dispersion of $TiO_2$ Particles

The dispersibility is evaluated from particle size measurements using the Coulter LS130.

Figure 2A:
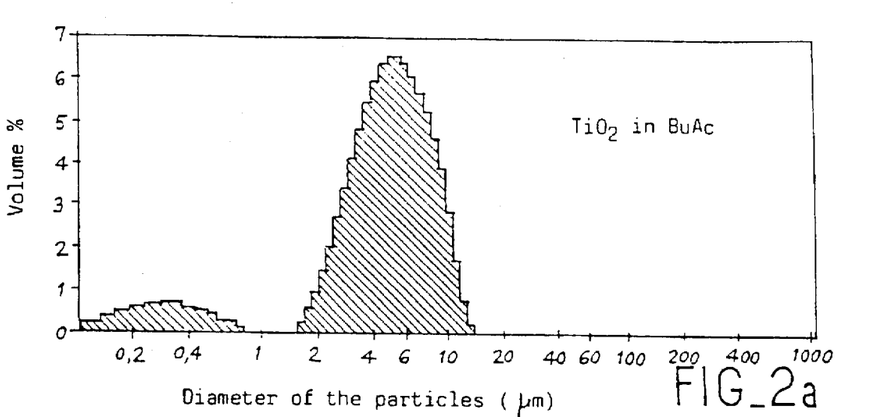
FIG. 2a illustrates the particle size distribution before the addition of copolymer to the organic solvent.
Figure 2B:
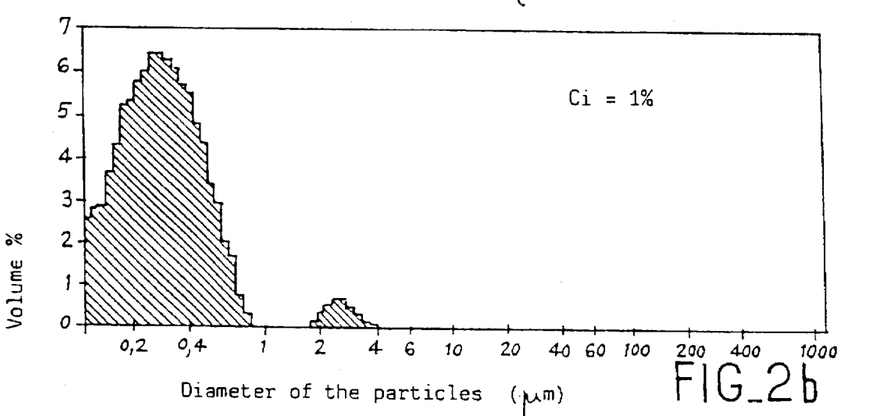
FIG. 2b illustrates the particle size distribution after the addition of copolymer where the initial concentration of the copolymer is 1%.
Figure 2C:
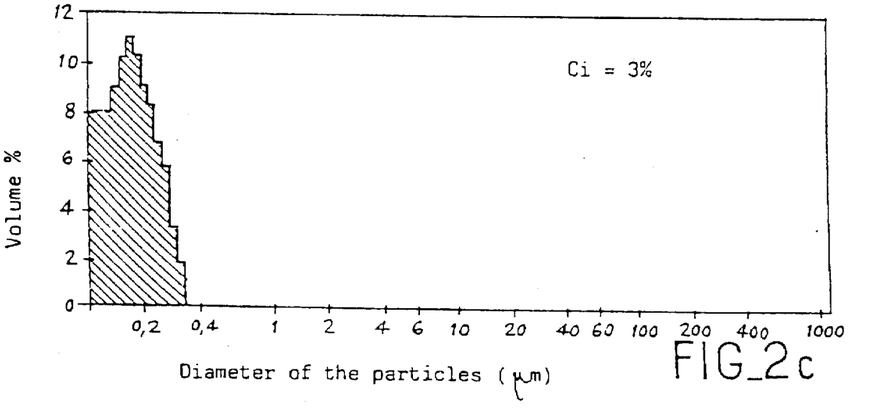
FIG. 2c illustrates the particle size distribution after the addition of copolymer where the initial concentration of the copolymer is 3%.

FIGS. 2a, 2b and 2c show the particle size analysis diagrams obtained using the Coulter LS130 apparatus for $TiO_2$ at different stages of the treatment for the same example as the adsorption isotherm given in Example 1. The copolymer affords a considerable reduction in the aggregates up to the point of causing them to disappear when the TiO$_2$ is totally covered (i.e. for initial polymer concentrations corresponding to the isotherm plateau).

For this type of example, a very good dispersing agent has to reduce the amount of aggregates to a value below 1%.

FIG. 2a shows the predominance of aggregates in the absence of copolymer in the solution.

FIG. 2b, which corresponds to an initial copolymer concentration Ci of 1% in butyl acetate, i.e. 3.33% based on TiO$_2$, shows that there is already a distinct regression of the proportion of aggregates even before the plateau.

FIG. 2c, which relates to conditions corresponding to the isotherm plateau, in this instance an initial concentration Ci of 3%, shows the complete disappearance of aggregates.

Example 4

Demonstration of the Stabilization of a Particle Dispersion

The sedimentation rate of the three suspensions studied in Example 3 is studied by measuring the height of the inter-phase as a function of time.

Figure 3:
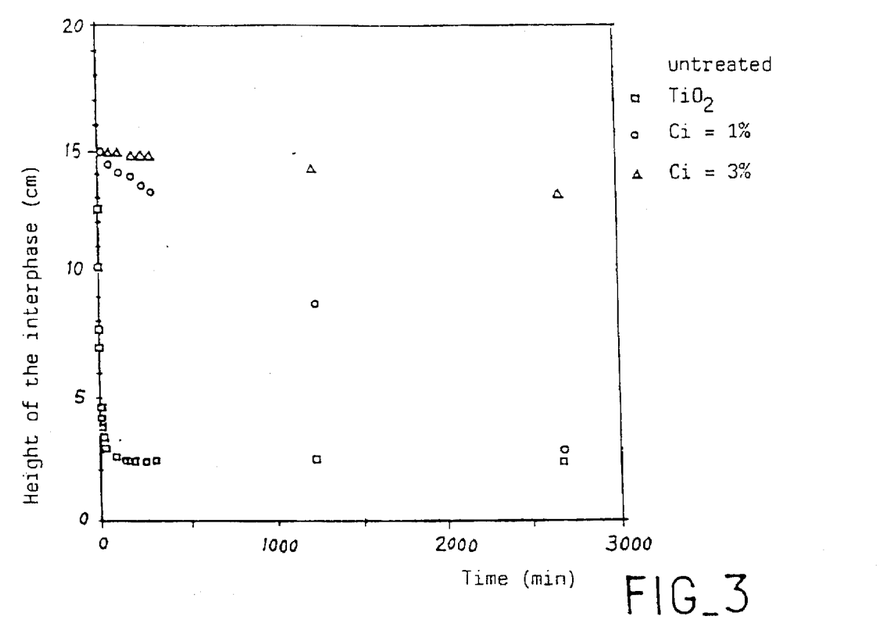
FIG. 3 illustrates the stability over time of the three solutions reported in FIGS. 2a, 2b, and 2c based on the height of the interphase.

FIG. 3 gives the height (in cm) of the inter-phase of the suspensions in tubes as a function of time for each of the suspensions corresponding respectively to:

- a suspension of TiO$_2$ in the absence of block copolymer (untreated TiO$_2$),
- a suspension before the isotherm plateau (Ci=1%), and
- a suspension on the isotherm plateau (Ci=3%).

Example 5

Demonstration of Stabilization

This Example again demonstrates the stabilization of the same suspension of TiO$_2$ powder as in the previous Examples by studying the variation in the absorbance of the supernatant as a function of the centrifugation time at 120 rpm (Shimadzu SA—CP3).

Figure 4:
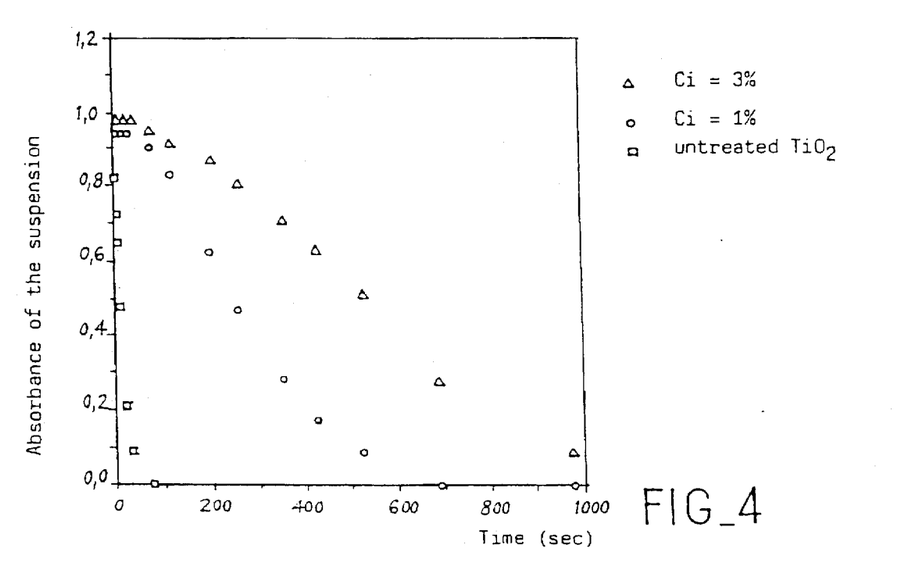
FIG. 4 illustrates the stability over time of the three solutions reported in FIGS. 2a, 2b, and 2c based on absorbents.

FIG. 4 gives the results obtained on the one hand with TiO$_2$ in butyl acetate in the absence of block copolymer, and on the other hand in the presence of PAA-b-PMMA before and on the isotherm plateau, under the same conditions as in the previous Examples (Ci=1% and Ci=3%).

Example 6

Demonstration of Stabilization in the Presence of Nitrocellulose

The height of the interphase in sedimentation tubes is studied as a function of time for suspensions in a 20% by weight solution of nitrocellulose (type CA4 SNPE) in butyl acetate, which reflects the sedimentation rate of the solid particles.

Figure 5:
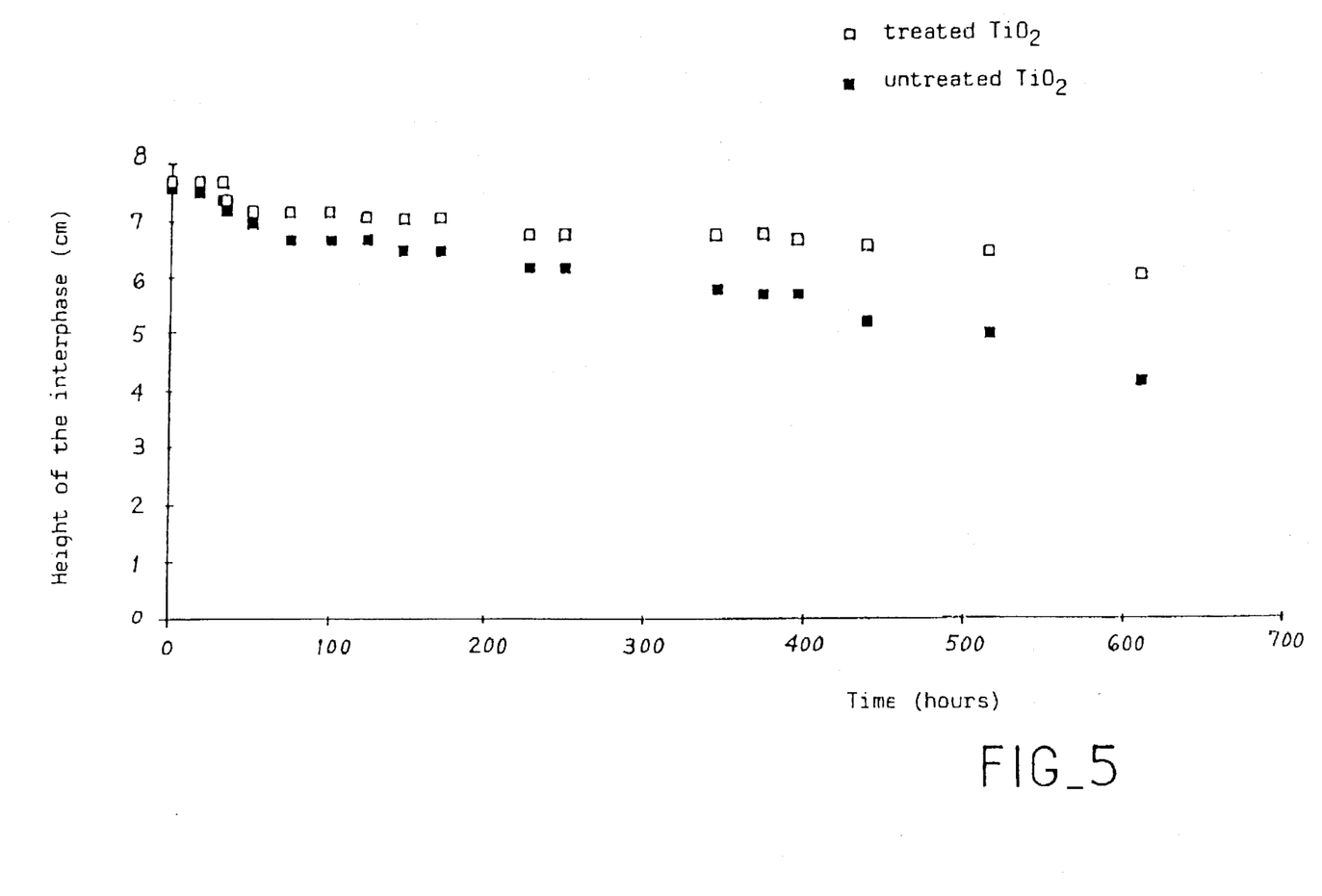
FIG. 5 illustrates the stability of treated and untreated particles where the initial copolymer concentration is 3% for the treated particles.

FIG. 5 makes it possible to compare the behavior of untreated TiO$_2$ with TiO$_2$ treated with a copolymer of Mn=45,000, containing 18% by weight of PAA (for the treatment Ci=3%).

Example 7

Demonstration of the Dispersing and Stabilizing Role of the Copolymers PAA-b-PMMA with Respect to TiO$_2$ (S=10 m$^2$/g)

The Table below collates the dispersion and stabilization results obtained for TiO$_2$ (S=10 m$^2$/g) and a series of copolymers PAA-b-PMMA (Ci=3%).

The aggregates consist of particles with a size greater than 1 μm. In the case of crude TiO$_2$, the aggregates represent 88.4% by volume.

The Shimadzu index is the time (in seconds) required for the absorbance to change from 100% to 50%. By way of reference, this index is 15 for untreated TiO$_2$.

| Total Mn of PAA-b-PMMA | % by weight of PAA | Ci = 3% for the treatment of TiO$_2$ | |
|---|---|---|---|
| | | Dispersion % of aggregates (by vol) | Stabilization Shimadzu index |
| 2300 | 34.2 | 0 | / |
| 9900 | 22 | 0 | 600 |
| 16500 | 22.5 | 0 | 532 |
| 17900 | 32.3 | 0 | 530 |
| 18900 | 36 | 18.4 | 300 |
| 29800 | 14.5 | 0 | 463 |
| 31100 | 35 | 0 | 435 |
| 34800 | 25.8 | 31.7 | 194 |
| 52400 | 26.7 | 0 | 607 |
| 57000 | 31.8 | 35.2 | 200 |
| 59700 | 49.7 | 23.2 | 233 |

Example 8

Demonstration of the Dispersing Effect of the Copolymers in Different Media The dispersion of two pigments, consisting respectively of a yellow iron oxide powder of mean particle size 0.4 μm and specific surface area 20 m$^2$/g and a titanium oxide powder of specific surface area 10 m$^2$/g, is studied successively, the 4 mixtures below, for each of the two pigments, being dispersed for one hour in a ball mill of the Red Devil type, used in paint.

The mixtures produced are as follows, the percentages being given by weight:

mixture 1 (comparative):
  pigment: 20%
  butyl acetate: 80% mixture 2:
  pigment: 20%
  copolymer of Example 1: 5%
  butyl acetate: 75% mixture 3:
  pigment: 20%
  copolymer of Example 1: 5%
  grinding aid (Neocryl B 1000): 5%
  butyl acetate: 70% mixture 4:
  pigment: 20%
  copolymer of Example 1: 5%
  nitrocellulose: 5%
  butyl acetate: 70%

The different mixtures are observed under the optical microscope and show, for both the pigments studied, that the dispersion of mixtures 2 to 4 is better than that of mixture 1.

Example 9

Preparation of a Nail Varnish

Colorless bases of the following composition are used:

| | |
|---|---|
| nitrocellulose | 10 to 15% |
| filler resin: arylsulfamide | 8 to 12% |
| plasticizer: dibutyl phthalate, camphor | 6 to 8% |
| solvents: ethyl acetate, butyl acetate, toluene | 65 to 75% |
| suspending agent: bentone | 0.8 to 1.5% |
| additives | 1 to 2% |

Nail varnishes are prepared by the following procedure starting from one of the mixtures 2 to 4 of Example 8:

The mixture is diluted with one of the above colorless bases until a coloring solution containing about 5% by weight of pigment is obtained, and the product obtained is then mixed with one of the above colorless bases, in proportions depending on the desired color, to give about 1% by weight of pigment in the finished varnish.

What is claimed is:

1. A method for improving the wettability of solid particles in an essentially aqueous free organic solvent, comprising the step of: introducing into said solvent containing said solid particles an effective amount of an AB block copolymer comprising at least one block A which is a polymer of acrylic or methacrylic acid and at least one block B which is a polymer of an alkyl acrylate or methacrylate with the alkyl chain being between $C_1$ and $C_{10}$, said block B being soluble in said solvent and said block A representing less than 50% by weight of said copolymer.

2. The method according to claim 1, wherein said block copolymer is a two-block copolymer (A-b-B) or a three-block copolymer (A-b-B-b-A or B-b-A-b-B).

3. The method according to claim 1, wherein said block copolymer is a two-block copolymer wherein said block A is a polymer of acrylic acid (symbolized by AA) and said block B is a polymer of methyl methacrylate (symbolized by MMA), said block copolymer represented by PAA-b-PMMA.

4. The method according to claim 1, wherein the particles have dimensions between 50 nm and 100 µm.

5. The method according to claim 1, wherein said particles are mineral particles.

6. The method according to claim 1, wherein said particles are metal oxide particles.

7. The method according to claim 1, wherein said particles are pigments which may or may not be fixed to an organic or mineral support.

8. The method according to claim 1, wherein said particles are titanium dioxide ($TiO_2$).

9. The method according to claim 1, wherein the copolymer has a number-average molecular weight ($M_n$) of between 2,000 and 500,000.

10. The method according to claim 1, wherein the block A of said copolymer represents 5 to less than 50% by weight of said copolymer.

11. A method for obtaining a stable dispersion of solid particles in an essentially aqueous free organic solvent, comprising the step of introducing into said solvent an effective amount of an AB block copolymer comprising at least one block A, which is a polymer of acrylic or methacrylic acid and at least a block B, which is a polymer of an alkyl acrylate or methacrylate with the alkyl chain being between $C_1$ and $C_{10}$), said block B being soluble in aid solvent or mixture of solvents and said block A representing less than 50% by weight of said copolymer.

12. The method according to claim 11, wherein said block copolymer is a two-block copolymer (A-b-B) or a three-block copolymer (A-b-B-b-A or B-b-A-b-B).

13. The method according to claim 11, wherein said block copolymer is a two-block copolymer wherein said block A is a polymer of acrylic acid (symbolized by AA) and said block B is a polymer of methyl methacrylate (symbolized by MMA), said AB block copolymer represented by PAA-b-PMMA).

14. The method according to claim 11, wherein the particles have dimensions between 50 nm and 100 µm.

15. The method according to claim 11, wherein said particles are mineral particles.

16. The method according to claim 11, wherein said particles are metal oxide particles.

17. The method according to claim 11, wherein said particles are pigments which may or may not be fixed to an organic or mineral support.

18. The method according to claim 11, wherein said particles are titanium dioxide ($TiO_2$).

19. The method according to claim 11, wherein the copolymer has a number-average molecular weight ($M_n$) Of between 2,000 and 500,000.

20. The method according to claim 11, wherein the block A of said copolymer represents 5 to less than 50% by weight of said copolymer.

21. A stable dispersion of solid particles in an essentially aqueous free organic solvent, wherein a dispersing agent is an AB block copolymer comprising at least one block A, which is a polymer of acrylic or methacrylic acid and at least one block B, which is a polymer of an alkyl acrylate or methacrylate with the alkyl chain being between $C_1$ and $C_{10}$, said block B being soluble in aid solvent and said block A representing less than 50% by weight of said copolymer.

22. The dispersion according to claim 21, wherein said particles have dimensions between 50 nm and 100 µm.

23. The dispersion according to claim 21, wherein said particles are mineral particles.

24. The dispersion according to claim 21, wherein said mineral particles are mineral oxide particles.

25. The dispersion according to claim 21, wherein said particles are pigments which may or may not be fixed to an organic or mineral support.

26. The dispersion according to claim 21, wherein said particles are titanium dioxide ($TiO_2$).

27. The dispersion according to claim 21, wherein the block copolymer has a number-average molecular weight ($M_n$) of between 2,000 and 500,000.

28. The dispersion according to claim 21, wherein the block copolymers have a concentration of between 0.1 and 30% by weight based on the weight of the solid particles.

29. The dispersion according to claim 21, wherein the solvent is selected from the group consisting of esters, and ester/alcohol mixtures consisting predominantly of ester.

30. The dispersion according to claim 21, wherein said solvent is butyl acetate or a butyl acetate/ethanol mixture containing at least 50% of butyl acetate.

31. A nail varnish composition of improved stability containing a dispersion of solid particles in an essentially aqueous free organic solvent, and a dispersing agent comprising an AB block copolymer comprising at least one block A which is a polymer of acrylic or methacrylic acid and at least one block B which is a polymer of an alkyl acrylate or methacrylate with the alkyl chain being between $C_1$ and $C_{10}$, said block B being soluble in said solvent and said block A representing less than 50% by weight of said copolymer.

32. The nail varnish composition according to claim 31, wherein said block copolymer is a two-block copolymer (A-b-B) or a three-block copolymer (A-b-B-b-A or B-b-A-b-B).

33. The nail varnish composition according to claim 31, wherein said block copolymer is a two-block copolymer wherein said block A is a polymer of acrylic acid (symbolized by AA) and said block B is a polymer of methyl methacrylate (symbolized by MMA), said block copolymer represented by PAA-b-PMMA.

34. The nail varnish composition of claim 31 further comprising nitrocellulose.

35. The nail varnish composition of claim 31, wherein said solid particles have dimensions between 50 nm and 100 µm.

36. The nail varnish composition of claim 31, wherein said solid particles are selected from the group consisting of titanium oxide, zinc oxide, iron oxide, zirconium oxide, silica, alumina and calcium carbonate having a size ranging between 50 nm and 100 µm.

37. The nail varnish composition of claim 31, wherein said solid particle is titanium dioxide ($TiO_2$) having a size ranging between 50 nm and 100 µm.

38. The nail varnish composition of claim 31, wherein the solid particles are titanium dioxide and said particles comprise about 1% by weight of said varnish composition.

* * * * *